United States Patent [19]

Müller et al.

[11] Patent Number: 5,006,655
[45] Date of Patent: Apr. 9, 1991

[54] PROCESS FOR THE PREPARATION OF TETRAHYDROFOLATES

[75] Inventors: Hans R. Müller, Schaffhausen; Martin Ulmann, Dachsen; Josef Conti, Schaffhausen, all of Switzerland; Günter Mürdel, Tengen-Büsslingen, Fed. Rep. of Germany

[73] Assignee: Eprova AG, Schaffhausen, Switzerland

[21] Appl. No.: 373,007

[22] Filed: Jun. 29, 1989

[30] Foreign Application Priority Data

Jun. 29, 1988 [DE] Fed. Rep. of Germany ....... 3821875

[51] Int. Cl.$^5$ .............................................. C07D 475/04
[52] U.S. Cl. ................................................... 544/258
[58] Field of Search ........................................ 544/258

[56] References Cited

U.S. PATENT DOCUMENTS 2,688,018  8/1954  Cosulich ........................... 544/258
4,959,472  9/1990  Wood et al. ........................ 544/258

FOREIGN PATENT DOCUMENTS 0266042  5/1988  European Pat. Off. ............. 544/258
3821875  2/1990  Fed. Rep. of Germany .
305574   2/1955  France .
0038285  3/1983  Japan ................................ 544/258
649550   5/1985  Switzerland .

OTHER PUBLICATIONS

Erteilungsbeschluss: German P 38 21 875.5-44 with English translation.
Chem. Abstracts, vol. 107, entry 214060w (1987).
Merck Index, 10th Edition (1983), entry 4111.
Russian article: Kaplan et al., Biologiceskie Nauki, vol. 7, pp. 33-37 (1987).
Fontecilla-Camps et al., *Chemistry and Biology of Pteridines*, p. 235, Elsevier/North Holland, N.Y.
Cosulich, Journal of the American Chemical Society, vol. 24, Aug. 20, 1952, No. 16, pp. 4125-4216.
Fontecilla-Camps et al., Journal of the American Chemical Society, 101:20/Sep. 26, 1979, pp. 6114-6115.
Feeney, Biochemistry, 1961, 20, 1837-1842.
Tetrahedron, vol. 42, No. 1, pp. 117-136, 1986, Rees et al.
J. Chem. Soc., Chem. Commun., 1987, pp. 470-472, Rees et al.
Kaufman et al, The Journal of Biological Chemistry, vol. 238, No. 4, Apr. 1963, pp. 1498-1500.
The Journal of Biological Chemistry, vol. 253, No. 1, Jan. 10, 1978, pp. 242-245, White et al.
Fachlexikon ABC Chemie, Stereoisomeric, p. 1077, 1987.
Rome, Analytical Biochemistry, 22, 166-177 (1986).
Analytical Biochemistry, 168, 398-404 (1988), Choi et al.
Folates and Pterins, vol. 1, Chemistry and Biochemistry of Folates, 1984, pp. xiii and 99.
Helvetica Chemica Acta-vol. 64, Fasc. 8 (1981)-No. 266, p. 2627, Kalbermatten et al.
Chem. Abstr., vol. 98, entry 215624r (1983).

*Primary Examiner*—Donald G. Daus
*Attorney, Agent, or Firm*—Millen, White & Zelano

[57] ABSTRACT

For the preparation of 5,10-methenyl-(6R)-, 5-formyl-(6S)- or 5-methyl-(6S)-tetrahydrofolic acid or salts thereof, 5,10-methenyl-(6R,S)-tetrahydrofolic acid, the inner salt thereof or one of the salts thereof with strong acids is subjected to diastereomer separation by fractional crystallization and, if desired, the resulting 5,10-methenyl-(6R)-tetrahydrofolic acid is converted by treatment with a hydrolyzing agent into 5-formyl-(6S)-tetrahydrofolic acid or by treatment with a reducing agent into 5-methyl-(6S)-tetrahydrofolic acid, and the resulting free acid may be converted into one of its salts by treatment with a base.

16 Claims, No Drawings

PROCESS FOR THE PREPARATION OF TETRAHYDROFOLATES

BACKGROUND OF THE INVENTION

The invention relates to a process for the preparation of 5,10-methenyl-(6R)-tetrahydrofolic acid [5,10-CH-(6R)-THF; "(6R)-I"], of biologically active tetrahydrofolates, especially of 5-formyl-[5-CHO-(6S)-THF] and 5-methyl-(6S)-tetrahydrofolic acid [5-Me-(6S)-THF] as well as of the salts thereof, especially the physiologically well tolerated calcium, magnesium, sodium and potassium salts thereof.

The said (6S)-tetrahydrofolates [(6S)-5,6,7,8-tetrahydropteroyl-L-glutamates] are the sufficiently stable natural biologically active forms of folic acid (folic acid cofactors).

5-CHO-(6S)-THF is the citrovorum factor (=growth factor for *Leuconostoc citrovorum*).

In the organism 5-CHO-(6S)-THF is converted into 5-Me-(6S)-THF via 5,10-methylene-(6R)-THF.

Tetrahydrofolates contain 2 asymmetric centers. When they are synthesized from folic acid [N-(pteroyl)-L-glutamic acid] the chiral C atom contained in the glutamic acid residue is in the L form, whereas the chiral C atom produced in position 6 [C(6)] by hydrogenation of the double bond in the 5,6 position of the pteroyl radical is present in the racemic, the (6R,S), form. Accordingly, all synthetic tetrahydrofolates consist of a 1:1 mixture of two diastereomers.

The tetrahydrofolates which occur naturally, for example in the liver, are found only in one diastereomeric form, with 5-CHO-THF being in the form of 5-CHO-(6S)-THF, and 5-Me-THF being in the form of 5-Me-(6S)-THF.

The absolute configuration at C(6) of natural tetrahydrofolic acid is, according to J. C. Fontecilla-Camps et al., J. Amer. Chem. Soc. 101 (20), 6114/5 (1979), in accordance with the sequence rule to be specified as S, and that at C (6) of natural 5,10-methylene-tetrahydrofolic acid and of 5,10-methenyl-tetrahydrofolic acid to be specified as R: R. Kalbermatten et al., Helv. chim. Acta 64 (8), 2627 (1981), footnote 4.

5-CHO-(6R,S)-THF (folinic acid) is used in the form of its calcium salt (leucovorin) as a pharmaceutical for the treatment of megaloblastic folate-deficiency anemia, as an antidote to increase the tolerability of folic acid antagonists, specifically of aminopterin, methotrexate and fluorouracil in cancer therapy ("leucovorin rescue") and the treatment of autoimmune diseases such as psoriasis and rheumatoid arthritis, as well as to increase the tolerability of certain antiparasitics, for example trimethoprim-sulfamethoxazole, in chemotherapy.

Calcium 5-methyl-(6R,S)-tetrahydrofolate is used similarly.

Administration of 5-CHO-(6R,S)-THF is followed by rapid conversion of the (6S) portion of this diastereomeric mixture into 5-Me-(6S)-THF, whereas the (6R) portion is not metabolized: J. A. Straw et al., Cancer Research 44, 3114–3119 (1984).

In addition, 5-CHO-(6R)-THF inhibits some of the enzymes responsible for $C_1$ transfer and thus the biochemical action of the tetrahydrofolates: R. P. Leary et al., Biochem. Biophys. Res. Commun. 56, 484 (1973); V. F. Scott et al., ibid. 14, 523 (1964); G. K. Smith et al., Biochemistry, 20, 4034 (1981). Hence the use of (6S)-tetrahydrofolates in place of (6R,S)-tetrahydrofolates ought also to have therapeutic advantages.

There is therefore a need to replace the mixtures of diastereomers, containing the (6S) and (6R) forms in each case, which have hitherto been used, with the natural (6S) form.

Many attempts have been made to resolve (6R,S)-tetrahydrofolic acids and to carry out the asymmetric synthesis thereof and to isolate the physiologically active forms.

D. Cosulich et al., J. Amer. Chem. Soc. 74, 4215–16 (1952), U.S. Pat. No. 2,688,018 (Aug. 31, 1954), have attempted, for example, to bring about the resolution by fractional crystallization of an alkaline earth metal salt, for example the calcium or strontium salt, of 5-CHO-(6R,S)-THF from an aqueous solution [see also J. C. Fontecilla-Camps et al., J. Amer. Chem. Soc. 101, 6114 (1979)].

The desired resolution cannot be achieved under the conditions published by B. Cosulich et al. On crystallization of, for example, the calcium salt of 5-CHO-(6R,S)-THF from water at pH 7–8 it is always the 6R,S form which is recovered, as can be demonstrated quantitatively by means of chromatographic analysis on a chiral HPLC column as well as on the basis of the optical rotation. It is immaterial in this connection whether crude or pure calcium salt of 5-CHO-(6R,S)-THF is used for the crystallization; the (6R,S) form is always recovered. Nor is it possible to resolve and enrich the (6S) form by seeding a supersaturated aqueous solution of an alkaline earth metal salt of 5-CHO-(6R,S)-THF with authentic alkaline earth metal salt of 5-CHO-(6S)-THF.

Resolution of the pairs of diastereomers has also been attempted by chromatography: J. Feeney et al., Biochemistry 20, 1837 (1981). In addition the (6S) isomers have been prepared by stereospecific reduction of dihydrofolates in the presence of dihydrofolate reductase: L. Rees et al., Tetrahedron 42, 117 (1986).

L. Rees et al., J. Chem. Soc. Chem. Commun. 1987, 470 and EP-A No. 2,266,042 have described a process for the resolution of (6R,S)-THF with which it was possible to produce small amounts of 5-CHO-(6S)-THF and 5-CHO-(6R)-THF. The process comprises reacting (6R,S)-THF with, for example, (−)-menthyl chloroformate to give the diastereomeric 5-(−)-menthyloxycarbonyl-tetrahydrofolic acids, separating these by repeated treatment with n-butanol, heating the resulting diastereomers with a saturated solution of hydrogen bromide in a mixture of formic acid and acetic acid, with formation after hydrolysis of 5-formyl-(6S)-and -(6R)-THF, and finally isolating the latter as calcium salts.

This process is laborious and difficult and requires highly toxic phosgene to prepare the chiral reagent. In addition, the starting material (6R,S)-THF is very unstable. On elimination of the chiral accessory group with HBr in AcOH at >50° C. there is partial elimination of the glutamic acid, and by-products which can be removed only with difficulty are formed. The (6S)-folinic acid produced by a process of this type would be so costly that it would be scarcely possible to use it in place of (R,S)-tetrahydrofolates.

No industrially utilizable process for obtaining (6S)-tetrahydrofolates has hitherto been disclosed. Thus, the object was still to find a straightforward and industrially applicable process for the preparation of 5-CHO- and 5-Me-(6S)-THF.

5-CHO- and 5-Me-(6R,S)-THF can be prepared in a known manner from folic acid. Formylation with formic acid produces 10-formyl-folic acid (10-CHO-FA). The latter can subsequently be catalytically hydrogenated to 10-formyl-tetrahydrofolic acid (10-CHO-THF). 5,10-Methenyl-tetrahydrofolic acid (I; 5,10-CH-THF; "anhydroleucovorin") can be obtained from the latter by dehydration:

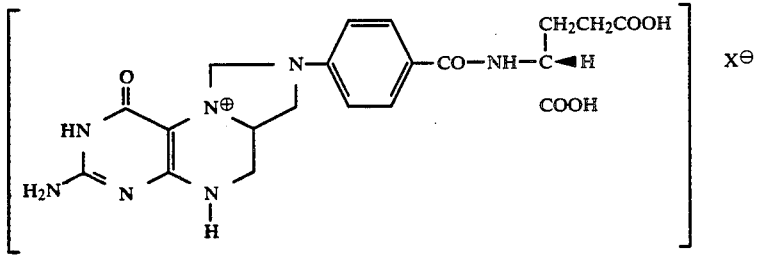

In this formula, X⊖ is one equivalent of any desired anion, for example Cl⊖ or Br⊖. I can also be in the form of an acid addition salt, for example the chloride hydrochloride of the abbreviated formula (5,10-CH-THF)⊕Cl⊖.HCl. The corresponding inner salt (I, X⊖ absent, COO⊖ in place of COOH) can also be obtained from the latter form with the aid of an anion exchanger.

The desired tetrahydrofolates can easily be prepared from I: hydrolysis (transformylation) results in 5-formyl-tetrahydrofolic acid (5-CHO-THF) which can be isolated as the calcium salt (leucovorin): Swiss Patent Specification No. 305,574 (CYANAMID). Reduction with sodium borohydride results in 5-methyl-tetrahydrofolic acid (5-Me-THF; mefolinic acid) which can be isolated as the calcium or magnesium salt: Swiss Patent Specification No. 649,550 (EPROVA).

SUMMARY OF THE INVENTION

It is an object of one aspect of the present invention to provide a process for preparing the desired tetrahydrofolates, or salts thereof, in substantially pure form, free from the undesirable 6-diastereomers thereof.

An object of a further aspect is to provide substantially pure 5,10-methenyl-(6R), 5-methyl-(6S)- or 5-formyl-(6S)-tetrahydrofolic acid, or a salt thereof.

Upon further study of the specification and appended claims, further objects and advantages of this invention will become apparent to those skilled in the art.

To attain such objects, there is provided a process for the preparation of 5,10-methenyl-(6R)-, 5-formyl-(6S)- or 5-methyl-(6S)-tetrahydrofolic acid, or a salt thereof in a form substantially free of its 6-diastereomer, comprising the step of fractionally crystallizing 5,10-methenyl-(6R,S)-tetrahydrofolic acid, the inner salt thereof or one of the salts thereof with strong acids, to obtain substantially pure 5,10-methenyl-(6R)-tetrahydrofolic acid. The invention further relates to a process for hydrolyzing the resulting 5,10-methenyl-(6R)-tetrahydrofolic acid by treatment with a hydrolyzing agent to obtain substantially pure 5-formyl-(6S)-tetrahydrofolic acid or a salt thereof. The invention further relates to a process for reducing the resulting 5,10-methenyl-(6R)-tetrahydrofolic acid by treatment with a reducing agent to obtain substantially pure 5-methyl-(6S)-tetrahydrofolic acid or a salt thereof. In each of these processes, the resulting free acid may be converted into one of its salts by treatment with a base.

This invention further provides substantially pure 5,10-methenyl-(6R)-, 5-formyl-(6S)-, or 5-methyl-(6S)-tetrahydrofolic acid, or a salt thereof, produced by the process of this invention. In this context, substantially pure generally means a concentration of the preferred compound of >95 weight percent, preferably >99 weight percent.

It has now been found, surprisingly, that upon fractional crystallization of solutions of (6R,S)-I or of the salts thereof, (6R)-I, the acid addition salts thereof (of the abbreviated formula [5,10-CH-(6R)-THF]+X−.HX), or the inner salt thereof, can be induced to crystallize in such a manner that the crystals contain more than 90% (6R)-I. (6R)-I in turn is very suitable for the preparation of the desired tetrahydrofolates: from it are obtained 5-CHO-(6S)-THF by hydrolysis and 5-Me-(6S)-THF by reduction.

Thus, the crucial point is that the diastereomer separation is carried out at the stage of I.

The success of this fractionation is surprising because Rees et al., J. Chem. Soc. Chem. Commun. 1987, 470, incorporated an additional chiral center in the THF molecule to make the resolution possible, and thus introduced a considerable complication.

The diastereomer separation according to the invention is preferably carried out by fractional crystallization from at least one polar solvent.

Examples of suitable polar solvents are: lower aliphatic carboxylic acids (e.g., $C_1$–$C_4$), especially formic acid as well as acetic acid, volatile water-soluble amides such as formamide, dimethylformamide, dimethylacetamide, 1-methylpyrrolidone, 2-piperidinone, 4-formylmorpholine, 1-formylpyrrolidone, 1-formylpiperidine and tetramethylurea, sulfoxides or sulfones such as dimethyl sulfoxide, dimethyl sulfone or sulfolane (tetramethylene sulfone), concentrated aqueous strong acids such as 20–35% strength hydrochloric acid or other aqueous mineral acids, such as, for example, hydrobromic acid, hydriodic acid, sulfuric acid, nitric acid or phosphoric acid, or solutions of strong organic acids such as of oxalic acid, maleic acid, trichloroacetic acid, trifluoroacetic acid, methanesulfonic acid, benzenesulfonic acid, toluenesulfonic acid and camphorsulfonic acids. Formic acid is preferred.

However, mixtures of the above-mentioned solvents are suitable and preferred, especially mixtures of one of the organic "solvents" mentioned with an aqueous mineral acid or with water ("crystallizing agent"). It is also possible to use a concentrated aqueous mineral acid, for example concentrated hydrochloric acid, as solvent, and a small amount of water as crystallizing agent. If the amount of water approaches or even equals that of the concentrated aqueous mineral acid, then [5,10-(6R,S)-THF]+X−.HX crystallizes out, that is to say no resolution takes place. The preferred solvent is formic acid, and the preferred crystallizing agent is an aqueous strong acid, especially dilute hydrochloric acid, hydrobromic acid, sulfuric acid, a sulfonic acid or nitric acid. An aqueous strong acid is generally defined as an aqueous acid having a dissociation constant (pK$_s$) at 20° C. of less than 2, preferably less than 0. It is also possible to use glacial acetic acid in place of an aqueous strong acid as crystallizing agent.

The final product obtained as a rule is an acid addition salt of the 5,10-methenyl-(6R)-tetrahydrofolic acid salt I with the corresponding acid HX. If, for example, aqueous concentrated hydrochloric acid ("crystallizing agent") is added to a concentrated solution of the hydrochloride of (6R,S)-I (X=Cl) in formic acid ("solvent"), then (6R)-I crystallizes out in the form of the chloride hydrochloride of the abbreviated formula [5,10-CH-(6R)-THF]Cl.HCl with a (6R) content of about 90%. This (6R) content can be increased by another recrystallization, for example from formic acid/hydrochloric acid. The hydrobromide of (6R)-I (X=Br), for example, is obtained analogously if hydrobromic acid is added to a solution of the hydrobromide of (6R,S)-I (X=Br) or of the inner salt of (6R,S)-I in formic acid.

The acid concentration and the ratios of amounts of solvent and crystallizing agent can be varied within wide limits. It is preferable for the concentration of 5,10-CH-(6R,S)-THF to be between 10 and 40% by weight, and for the ratio between solvent and crystallizing agent to be between 10:1 and 1:1. The acid concentration in the crystallizing agent can be between 0 and 12N. As a rule, higher yields with a poorer resolving effect are achieved if a relatively large quantity of crystallizing agent is used; on the other hand, if little crystallizing agent is employed, the resolving effect is better although the yield may fall. The optimal reaction conditions, which depend on the intended aim, the particular starting material, the solvent and the crystallizing agent, can be determined without difficulty by systematic tests.

If the starting material is an acid addition salt of the type [5,10-CH-(6R,S)-THF]X.HX, it may even be possible to separate the diastereomers with the formation of [5,10-CH-(6R)-THF]X.HX merely by fractional crystallization from a solvent such as formic acid with the addition of water, or even without any addition of a crystallizing agent.

As a rule, the desired (6R) compound crystallizes out first; the diastereomeric (6S) compound becomes enriched in the filtrates. In a few cases, for example when the inner salt of 5,10-CH-(6R,S)-THF is crystallized from formic acid/water or when [5,10-CH-(6R,S)-THF]. trichloroacetate is crystallized from dimethyl sulfoxide by contrast the (6S) diastereomer separates out first, while the (6R) diastereomer can be isolated from the filtrate.

A particularly preferred embodiment of the invention comprises adding a strong aqueous acid, for example hydrochloric acid, to a formic acid solution of (6R,S)-I produced in situ by formylation of folic acid to 10-formyl-folic acid and subsequent catalytic hydrogenation and dehydration; it is possible in this way to induce the crystallization of the (6R) diastereomer in the form of the acid addition salt of the formula [5,10-CH-(6R)-THF]X.HX, for example the corresponding chloride hydrochloride.

This process has made the (6S)-tetrahydrofolates, especially 5-CHO-(6S)-THF and 5-Me-(6S)-THF, accessible in a very straightforward and especially economic manner.

Primarily suitable as physiologically well tolerated salts are the calcium, magnesium, sodium and potassium salts.

The magnesium salts are distinguished by, in general, being more soluble in water compared with the calcium salts. This permits a wider dose range when they are used.

In order to obtain optically pure 5-CHO- and 5-Me-(6S)-THF it is unnecessary completely to remove concomitant (6S) form from 5,10-CH-(6R)-THF or the acid addition salts thereof. The residual amount of "wrong" diastereomer is eliminated in each case on conversion of 5,10-CH-(6R)-THF by hydrolysis or reduction into 5-CHO-(6S)-THF or 5-Me-(6S)-THF and the isolation thereof, as it remains in the mother liquor. Thus by employing crude 5,10-CH-(6R)-THF, containing from 10 to 25% of 5,10-CH-(6S)-THF, for the hydrolysis or reduction process, the total yield of optically pure 5-CHO- and 5-Me-(6R)-THF is substantially increased, as the losses incurred with an additional fractional crystallization of the crude 5,10-CH-(6R)-THF are avoided.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and the following examples, all temperatures are set forth uncorrected in degrees Celsius and, unless otherwise indicated, all parts and percentages are by weight.

The entire texts of all applications, patents and publications, if any, cited above and below, and of corresponding Application No. P 38 21 875.5 filed June 29, 1988 in the Federal Republic of Germany, are hereby incorporated by reference.

EXAMPLES

Example 1

Calcium 5-formyl-(6S)-tetrahydrofolate 1.1 Fractional crystallization of 5,10-methenyl-(6R,S)-tetrahydrofolic acid [anhydro-leucovorin; (6R,S)-I)]

300 ml of 2N hydrochloric acid are added to a solution of 1000 g of [5,10-methenyl-(6R,S)-tetrahydrofolic acid]chloride.hydrochloride.dihydrate ([5,10-CH-(6R,S)-THF]Cl.HCl.2H$_2$O) in 2 liters of formic acid at 35° C., and the mixture is slowly cooled to 20° C. and left to crystallize. The product which has separated out after some hours is filtered off and washed with 2N hydrochloric acid (6R)-I is obtained with a content of 91.5% of the [5,10-CH-(6R)-THF]Cl.HCl diastereomer, determined by HPLC using a chiral column (Resolvosil BSA-7).

$[\alpha]_D^{25} = +36°$ (c=1 in DMSO/2N HCl 8:2).

1.2 Conversion into calcium 5-formyl-(6S)-tetrahydrofolate (transformylation)

120 g of the crystals obtained as in 1.1 are dissolved in aqueous sodium hydroxide solution, boiled gently at pH 5.5 to 6.5 for some hours and cooled, and excess calcium chloride added. The calcium salt of 5-CHO-(6S)-THF which has separated out is recrystallized from water. Calcium 5-formyl-(6S)-tetrahydrofolate.5H$_2$O is obtained. Content of Ca 5-CHO-(6S)-THF $\geq 99\%$ area determined by HPLC using a chiral column.

$[\alpha]_D^{22} = -15°$ (based on anhydrous Ca salt; c=1.5% in water.

Example 2

5-Methyl-(6S)-tetrahydrofolic acid and calcium 5-methyl-(6S)-tetrahydrofolate 2.1. Fractional crystallization of (6R,S)-I obtained in situ A solution obtained by catalytic hydrogenation of 10-formyl-folic acid in formic acid is concentrated by evaporation to a content of about 30–35%. About 0.4 part by weight of concentrated (35% strength) hydrochloric acid is added to one part by weight of the concentrate at 35° C. The mixture is left to cool to room temperature and to stand at 5°–10° overnight, and the crystals which have separated out are filtered off and washed with a little ice-cold hydrochloric acid and acetone. [5,10-CH-(6R)-THF]Cl.HCl is obtained; (6R) content: 90%.

2.2 Recrystallization of crude [5,10-CH-(6R)-THF]Cl.HCl 1.2 kg of the crystals obtained as in 2.1 are dissolved in 3 liters of formic acid at 35° C., 450 ml of 2N hydrochloric acid are added, and the mixture is cooled gradually to room temperature and maintained at 0°–5° C. for some hours. The crystals which have formed are filtered off and washed with dilute hydrochloric acid and acetone. [5,10-CH-(6R)-THF]Cl.HCl.2H$_2$O with a (6R) content of 98% is obtained.

2.3 5-Methyl-(6S)-tetrahydrofolic acid [5-Me-(6S)-THF]

30 g of the [5,10-CH-(6R)-THF]Cl.HCl.2H$_2$O obtained as in 2.2 are introduced into a solution of 25 g of sodium borohydride and 3.4 g of tris in 300 ml of water, and the mixture is stirred overnight. The resulting solution is acidified to pH 4 with hydrochloric acid, whereupon 5-Me-(6S)-THF separates out as the dihydrate. It is filtered off and washed with water.

2.4 Calcium 5-methyl-(6S)-tetrahydrofolate

Half of the 5-Me-(6S)-THF.2H$_2$O obtained as in 2.3 is dissolved in the minimum amount of dilute sodium hydroxide solution, and the solution is treated with active charcoal and filtration aid and filtered, and excess calcium chloride is added. The calcium 5-methyl-(6S)-tetrahydrofolate pentahydrate which is formed gradually separates out. The product is left to crystallize at 0°–3° C. and is then filtered off and recrystallized from water.

$[\alpha]_D^{25} = +40°$ (based on the anhydrous compound; c=1.5% in water).

The same compound is also obtained when the [5,10-CH-(6R)-THF]Cl.HCl obtained as in Example 1.1 is further reacted as in Example 2.3/2.4.

Example 3

Magnesium 5-methyl-(6S)-tetrahydrofolate

The other half of the 5-Me-(6S)-THF obtained as in Example 2.3 is gradually dissolved in the minimum amount necessary of 2N sodium hydroxide solution, and an excess of magnesium chloride is added. The magnesium salt is induced to crystallize by addition of ethanol. This new compound is readily soluble in water.

Example 4

[5,10-CH-(6R)-THF]Cl.HCl 4.1 Fractional crystallization of [5,10-CH-(6R,S)-THF]Cl.HCl from formic acid 25 g of [5,10-CH-(6R,S)-THF]Cl.HCl.2H$_2$O are dissolved in 50 ml of formic acid at 35° C., and the solution is cooled to 0° C. and seeded with a trace of the product obtained as in Example 2.2. The [5,10-CH-(6R)-THF]Cl.HCl obtained after some hours is filtered off; (6R) content 79%. Renewed recrystallization increases the (6R) content to over 90%.

4.2 Selective crystallization of [5,10-CH-(6R)-THF]Cl.HCl by addition of water 25 g of [5,10-CH-(6R,S)-THF]Cl.HCl.2H$_2$O are dissolved in 50 ml of formic acid at 35° C., 5 ml of water are added, and the mixture is cooled to 0° C. and seeded with authentic (6R) isomer. The [5,10-CH-(6R)-THF]Cl.HCl obtained after standing overnight is filtered off; (6R) content: 86.5%.

4.3 Selective crystallization of [5,10-CH-(6R)-THF]Cl.HCl from aqueous hydrochloric acid 10 g of [5,10-CH-(6R,S)-THF]Cl.HCl.2H$_2$O are dissolved in 90 ml of concentrated hydrochloric acid at 50° C., and the solution is diluted with 10 ml of water and seeded at the same time with authentic material. [5,10-CH-(6R)-THF]Cl.HCl.2H$_2$O crystallizes out; 6R content: 87%.

Example 5

Preparation of the inner salt of 5,10-CH-(6R,S)-THF and of salts of 5,10-CH-(6R,S)-THF with strong acids and of [5,10-CH-(6S)-THF]Br.HBr 5.1 Inner salt of 5,10-CH-(6R,S)-THF A solution of 200 g of [5,10-CH-(6R,S)-THF]Cl.HCl in 1000 ml of formic acid is allowed to percolate through a column packed with 1100 ml of anion exchanger resin (IRA-68). The effluent is evaporated under reduced pressure. The residue is dissolved in formic acid, and the solution is divided into several aliquots.

Ethanol is added to one part of the solution, whereupon the inner salt crystallizes out. It has a noticeable yellow color. It is very sparingly soluble in water, organic solvents and even in polar solvents with the exception of formic acid.

The inner salt of 5,10-CH-(6R,S)-THF can also be obtained when a concentrated solution of 5,10-CH-(6R,S)-THF obtained in situ as in Example 2.1 is induced to crystallize by addition of a lower alcohol, for example ethanol, or of a ketone, for example methyl propyl ketone.

5.2 Salts of 5,10-CH-(6R,S)-THF with strong acids

An excess of the desired acid in formic acid is added to aliquots of the solution obtained as in 5.1, and ethanol is added to precipitate. The resulting salts are filtered off.

The following are prepared using this method:
[5,10-CH-(6R,S)-THF]Br.HBr,
[5,10-CH-(6R,S)-THF]I.HI,
[5,10-CH-(6R,S)-THF]phosphate,
[5,10-CH-(6R,S)-THF]sulfate,
[5,10-CH-(6R,S)-THF]nitrate,
[5,10-CH-(6R,S)-THF]oxalate,
[5,10-CH-(6R,S)-THF]maleate,
[5,10-CH-(6R,S)-THF]toluene-4-sulfonate,
[5,10-CH-(6R,S)-THF]benzenesulfonate,

[5,10-CH-(6R,S)-THF]methanesulfonate,
[5,10-CH-(6R,S)-THF]trichloroacetate and
[5,10-CH-(6R,S)-THF]trifluoroacetate.

5.3 [5,10-CH-(6R)-THF]Br.HBr

Somewhat more than the calculated amount of 6N aqueous hydrobromic acid is added to a solution of 20 g of the inner salt of [5,10-CH-(6R,S)-THF] in 30 ml of formic acid, and the mixture is stirred at 20°–25° C. 5,10-Methenyl-(6R)-tetrahydrofolic acid]bromide hydrobromide separates out after some time; (6R) content: 89%.

[5,10-CH-(6R)-THF]Br.HBr is also obtained when [5,10-CH-(6R,S)-THF]Br.HBr is dissolved in formic acid, and 2N aqueous hydrobromic acid is added, or when the "racemic" bromide hydrobromide is fractionally crystallized from a little dimethyl sulfoxide (about 4 ml per g).

In the case of acid addition salts with hydrohalic acids, nitric acid, sulfuric and sulfonic acids it is possible for two equivalents of acid per mole of 5,10-CH-THF to be involved in the salt formation. In the case of salts with moderately strong acids, for example maleic acid, only one equivalent of acid is bound in the salt form in each case.

Example 6

[5,10-CH-(6R)-THF]I.HI

This compound is prepared in analogy to Example 5.

Example 7

[5,10-CH-(6R)-THF]phosphate 30 g of [5,10-CH-(6R,S)-THF]phosphate, prepared as in Example 5, are dissolved in 80 ml of dimethyl sulfoxide at 50° C., and the solution is stirred at room temperature for some hours. [5,10-CH-(6R)-THF]phosphate crystallizes out after a lengthy period and is filtered off and dried.

6R isomer content: 70% (HPLC).

[5,10-CH-(6R)-THF]phosphate is also obtained when a small amount of 2M aqueous phosphoric acid is added to a solution of the racemic phosphate in formic acid.

Example 8

[5,10-CH-(6R)-THF]maleate 30 g of [5,10-CH-(6R,S)-THF]maleate are dissolved in 125 ml of 1-methyl-2-pyrrolidone at 50° C., and the solution is then stirred at room temperature. The [5,10-CH-(6R)-THF]maleate which separates out after a long time is filtered off; R content: 78%.

Example 9

[5,10-CH-(6R)-THF]toluene-4-sulfonate 15 g of [5,10-CH-(6R,S)-THF]toluene-4-sulfonate are dissolved in 28 ml of formic acid at 40°–50° C., 100 ml of water are added and the mixture is then stirred at room temperature. The [5,10-CH-(6R)-THF]toluene-4-sulfonate which has separated out is filtered off; 6R content: 85% (HPLC).

[5,10-CH-(6R)-THF]toluene-4-sulfonate is also obtained when the R,S compound is recrystallized from 1-methyl-2-pyrrolidone (about 4–6 ml/g) or dimethylacetamide or dimethyl sulfoxide (about 2–3 ml/g in each case).

Example 10

[5,10-CH-(6R)-THF]trichloroacetate

A solution of 10 g of [5,10-CH-(6R,S)-THF]trichloroacetate in 50 ml dimethyl sulfoxide is stirred for some hours and then filtered. The residue on the filter consists very predominantly of [5,10-CH-(6S)-THF]trichloroacetate. Water or ethanol is added to the filtrate, whereupon [5,10-CH-(6R)-THF]trichloroacetate separates out; 6R content: 70% (HPLC).

Example 11

Inner salt of 5,10-CH-(6S)-THF and of 5,10-CH-(6R)-THF 50 ml of water are added to a solution of 10 g of inner salt of 5,10-CH-(6R,S)-THF in 20 ml of formic acid, and the mixture is stirred at 20° C. for 17 hours.

The crystals which have separated out are filtered off. They consist predominantly of the inner salt of 5,10-CH-(6S)-THF. Content of 6S form: 73%. The content of 6S form is increased to 90% by repeating the operation. Acetone is added to the mother liquor, whereupon a second batch of crystals separates out. It is filtered off and examined. 75% of it consists of the inner salt of 5,10-CH-(6R)-THF.

Example 12

[5,10-CH-(6R)-THF]Cl.HCl 500 ml of water are added to a solution of 100 g of the inner salt of 5,10-CH-(6R,S)-THF in 200 ml of formic acid, and the mixture is stirred for 20 hours. The inner salt of 5,10-CH-(6S)-THF which has separated out is filtered off. Strong hydrochloric acid is added to the filtrate, or gaseous HCl is passed into the filtrate. The material which gradually separates out consists of [5,10-CH-(6R)-THF]Cl.HCl.2H$_2$O with a content of the 6R form of 95%.

Examples 13–18

The following can be prepared in a manner similar to that described in Examples 5 to 12:
13. [5,10-CH-(6R)-THF]nitrate,
14. [5,10-CH-(6R)-THF]sulfate,
15. [5,10-CH-(6R)-THF]oxalate,
16. [5,10-CH-(6R)-THF]methanesulfonate,
17. [5,10-CH-(6R)-THF]benzenesulfonate,
18. [5,10-CH-(6R)-THF]trifluoroacetate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the preparation of 5,10-methenyl-(6R)-, 5-formyl-(6S)-, or 5-methyl-(6S)-tetrahydrofolic acid, or a salt thereof, the latter two from the former, in a form substantially free of its 6-diastereomer, the step of fractionally crystallizing 5,10-methenyl-(6R,S)-tetrahydrofolic acid or a strong acid salt thereof, to obtain substantially enriched 5,10-methenyl-(6R)-tetrahydrofolic acid or a salt thereof with a non-reactive strong acid, wherein said substantially enriched 5,10-methenyl-(6R)-tetrahydrofolic acid or said salt thereof is present in at least a 70% by weight concentration.

2. A process of claim 1, wherein the fractional crystallization is carried out in at least one polar solvent.

3. A process of claim 2, wherein the polar solvent is an organic solvent and an aqueous non-reactive strong acid or water is added as a crystallizing agent to initiate crystallization.

4. A process of claim 2, wherein the polar solvent is a concentrated aqueous non-reactive mineral acid and water is added as a crystallizing agent to initiate crystallization.

5. A process of claim 3, wherein the polar solvent is formic acid and the crystallizing agent is an aqueous strong non-reactive mineral acid or is glacial acetic acid.

6. A process of claim 1, further comprising hydrolyzing resultant 5,10-methenyl-(6R)-tetrahydrofolic acid to obtain substantially pure 5-formyl-(6S)-tetrahydrofolic acid, or a salt thereof.

7. A process of claim 1, further comprising reducing 5,10-methenyl-(6R)-tetrahydrofolic acid produced by fractional crystallization of racemic 5,10-methenyl-(6R,S)-tetrahydrofolic acid to obtain substantially pure 5-methyl-(6S)-tetrahydrofolic acid, or a salt thereof.

8. A method of claim 1, wherein the fractionally crystallized 5,10-methenyl-(6R)-tetrahydrofolic acid or salt thereof has a purity of at least 86.5%.

9. A method of claim 1, further comprising recrystallizing the fractionally crystallized 5,10-methenyl-(6R)-tetrahydrofolic acid or salt thereof.

10. A method of claim 9, wherein the recrystallized 5,10-methenyl-(6R)-tetrahydrofolic acid or salt thereof has a purity of at least 90%.

11. A method of claim 6, wherein the resultant 5-formyl-(6S)-tetrahydrofolic acid or salt thereof has a purity of at least 98%.

12. A method of claim 7, wherein the resultant 5-methyl-(6S)-tetrahydrofolic acid or salt thereof has a purity of at least 98%.

13. In a process for the preparation of 5,10-methenyl-(6R)-, 5-formyl-(6S)-, or 5-methyl-(6S)-tetrahydrofolic acid, or a salt thereof, the latter two from the former, in a form substantially free of its 6-diastereomer, comprising the step of fractionally crystallizing an inner salt of 5,10-methenyl-(6R,S)-tetrahydrofolic acid to obtain substantially enriched 5,10-methenyl-(6R)-tetrahydrofolic acid or a salt thereof with a non-reactive strong acid, wherein an inner salt of 5,10-methenyl-(6S)-tetrahydrofolic acid with a non-reactive strong acid is first precipitated and removed, and then from resultant remaining mother liquor precipitating said inner salt of 5,10-methenyl-(6R)-tetrahydrofolic acid in a concentration of at least a 70% by weight.

14. A process according to claim 5, wherein the crystallizing agent is hydrochloric, hydrobromic or hydroiodic acid.

15. A process according to claim 2, wherein the solvent is formic acid.

16. A process according to claim 4, wherein the concentrated aqueous mineral acid is a hydrohalic acid.

* * * * *